United States Statutory Invention Registration [19]

[11] Reg. Number: H85

Shortsleeve [45] Published: Jul. 1, 1986

[54] BILE TUBE ASSEMBLY

[76] Inventor: Michael J. Shortsleeve, 753 Concord Ave., Belmont, Mass. 02178

[21] Appl. No.: 739,189

[22] Filed: May 30, 1985

[51] Int. Cl.[4] ..... A61M 25/00
[52] U.S. Cl. ..... 604/284
[58] Field of Search ..... 604/43, 284

[56] References Cited

U.S. PATENT DOCUMENTS 2,618,271 11/1952 Wallace ..... 604/284

FOREIGN PATENT DOCUMENTS 2454308 12/1980 France ..... 604/43

OTHER PUBLICATIONS

V. Mueller Catalogue 1963–p. 825.

*Primary Examiner*—Harold J. Tudor
*Attorney, Agent, or Firm*—Scott R. Foster

[57] ABSTRACT

A bile tube assembly for facilitating passage of bile from a bile duct to an external reservoir and for facilitating introduction of solutions from an external source to the bile duct.

5 Claims, 5 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BILE TUBE ASSEMBLY

BACKGROUND OF THE INVENTION

1. Field of the Invention

This invention relates to medical devices and is directed more particularly to a bile tube assembly for bile ducts.

2. Description of the Prior Art

When it is desired to permit egress of bile fluid from the bile duct to an external location, it is known to utilize a T-tube, the head of the T being disposed in bile duct, the axis of the T-head extending substantially axially of the bile duct, the T-head being tubular to permit ready passage therethrough. The stem portion of the T comprises a tubular portion extending from the T-tube head portion to an external location, to permit egress of excess bile by way of the T-tube stem portion.

On occasion, it is desirable to introduce solutions from an external source into the bile duct. To facilitate such in-flow of fluid, it is customary to run a smaller tube internally of the T-tube or, alternatively, to run the smaller tube alongside the exterior of the T-tube stem into the bile duct. In the first instance, there is often a problem in having the smaller tube proceed in the correct direction when it encounters the end of the T-tube stem portion in the area of the T-tube head portion. Often as not, the smaller tube proceeds in the wrong direction, necessitating repeated attempts. In the second instance, the smaller tube must proceed through an open wound in the body of the patient to reach its destination.

SUMMARY OF THE INVENTION

An object of the present invention is to provide a bile tube assembly which facilitates the out-flow of excess bile from the bile duct to an external reservoir and simultaneously permits the in-flow of solutions from an external source to the bile duct in a selected and preferred direction, without irritation to the body of the patient.

With the above and other objects in view, as will hereinafter appear, a feature of the present invention is the provision of a bile tube assembly comprising a first conduit having an elongated flexible tubular stem portion and at one end thereof an elongated flexible tubular head portion, the interior of the stem portion being in communication with the interior of the head portion, the head portion being adapted for disposition in a bile duct, and a second flexible conduit smaller in cross-sectional area than the first conduit, the second conduit being coextensive with and fixed to an interior wall of the first conduit stem portion and to an interior wall of the first conduit head portion, whereby to facilitate conveyance of fluid from an external source through the second conduit and into the bile duct while permitting, simultaneously, egress of bile from the bile duct through the first conduit head portion and stem portion to a distal end of the first conduit stem portion.

The above and other features of this invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention from which its novel features and advantages will be apparent. In the drawings.

DESCRIPTION OF THE PREFERRED EMBODIMENTS

Figure 1:
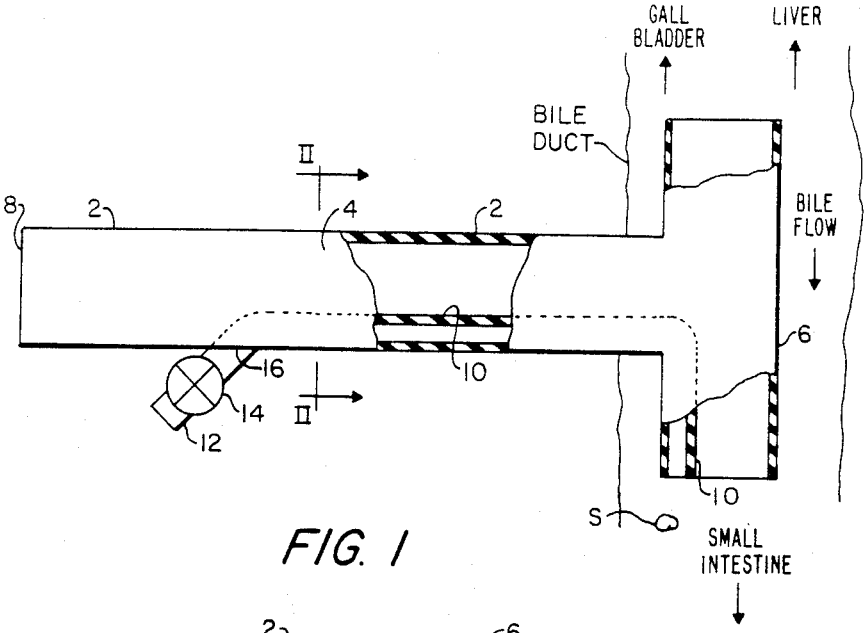
FIG. 1 is a front elevational, partly diagrammatic, view of one form of bile tube assembly, illustrative of an embodiment of the invention, portions of the assembly being broken away for clarity.
Figure 2:
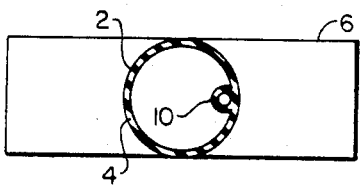
FIG. 2 is a sectional view thereof taken along line II—II of FIG. 1.

Referring to the drawings, it will be seen that the illustrative bile tube assembly includes a first conduit 2 having an elongated flexible tubular stem portion 4 of rubber, or other suitable soft, non-toxic material. At one end of the stem portion 4, there is disposed, transverse to the stem portion, a head portion 6, preferably of the same construction as the stem portion. The head and stem portions are in interior communication with each other and form interconnected passageways. The head portion 6 is adapted for disposition, surgically, in the bile duct of a patient, as is illustrated diagrammatically in FIG. 1. The head portion 6 of the first conduit 2 is disposed generally axially of the bile duct, aligned with the flow of bile. The stem portion 4 of the first conduit 2 extends outwardly to a location external of the patient.

When the pressure of the bile in the bile duct, and therefore in the head portion 6 of the first conduit becomes excessive, the bile travels through the stem portion 4 of the first conduit 2 and out a distal end 8 of the stem portion, into a reservoir (not shown).

The bile tube assembly further includes a second conduit 10, also of flexible, soft, non-toxic material, such as rubber, the second conduit having a substantially smaller cross-section than the first conduit 2 and being disposed within the first conduit 2. The second conduit is generally coextensive with and fixed to an interior wall of the first conduit stem portion and to an interior wall of the first conduit head portion. Preferably, the second conduit 10 and first conduit 2 are formed integrally as a single unit.

Figure 3:
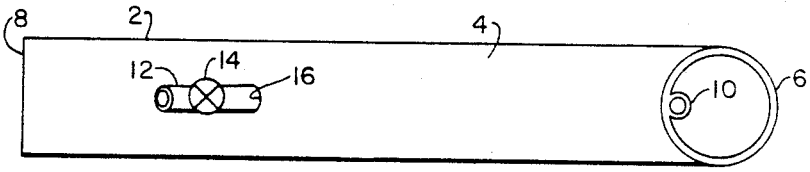
FIG. 3 is a side elevational, partly diagrammatic view thereof.

A distal end 12 of the second conduit 10 extends through an opening 16 in the wall of the stem portion 4 of the first conduit 2 and is provided with a valve 14, shown diagrammatically in FIGS. 1 and 3.

Figure 4:
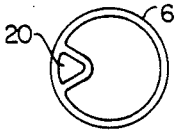
FIGS. 4 and 5 are partial side elevational views, illustrative of alternative embodiments.
Figure 5:
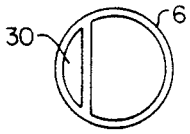

In FIGS. 4 and 5 there are shown alternative embodiments in which the second conduits 20 and 30, respectively, are of different cross-sectional configuration from that shown in FIG. 3.

In operation, the head portion 6 of the assembly is surgically implanted in a bile duct, as illustrated in FIG. 1. Typically, such would be the case following removal of the patient's gall bladder. When the flow of bile from the liver to the small intestine, through the bile duct, becomes excessive, the stem portion 4 permits egress of bile, as described above.

On occasion, cholelithiasis, stones in the gall bladder, may result in the passage of stones into the bile duct, as illustrated at "S" in FIG. 1. Upon the manifestation of symptoms of such a case, a dye may be introduced into the bile duct, by way of the second conduit 10, to assist in identifying the presence of stones. Once identified, stone dissolving solutions may be introduced into the bile duct, again using the second conduit, and discharged in a known direction in the bile duct, to bring the solution to bear upon the stones S. In like manner, other selected medications may be introduced in the bile duct.

The above-described introductions of solutions to the bile duct may be accomplished without disturbing the bile egress system defined by the first conduit.

It is to be understood that the present invention is by no means limited to the particular construction herein disclosed and/or shown in the drawings, but also comprises any modifications or equivalents within the scope of the disclosure. For example, the assembly may be provided with a third conduit similar to the second conduit, but disposed at the head end in a direction opposite to the second conduit, in the event it is desired to discharge a solution in an "upstream" direction in the bile duct.

Having thus described my invention what I claim as new and desire to secure by Letters Patent of the United States is:

1. A bile tube assembly comprising a first conduit having an elongated flexible tubular stem portion and at one end thereof an elongated flexible tubular head portion, the interior of the stem portion being in communication with the interior of the head portion, the head portion being adapted for disposition in a bile duct, and a second flexible conduit smaller in cross-sectional area than said first conduit, said second conduit being coextensive with and fixed to an interior wall of said first conduit stem portion and to an interior wall of said first conduit head portion, whereby to facilitate conveyance of fluid from an external source through said second conduit and into said bile duct, while permitting, simultaneously, egress of bile from said bile duct through said first conduit head portion and stem portion to a distal end of said first conduit stem portion.

2. The bile tube assembly in accordance with claim 1, in which said first conduit head portion extends transversely of said first conduit stem portion.

3. The bile tube assembly in accordance with claim 2 in which said first conduit is generally T-shaped.

4. The bile tube assembly in accordance with claim 1 in which said first conduit stem portion is provided with a hole therein proximate its distal end, and said second conduit extends through said hole and has a distal end external to said first conduit.

5. The bile tube assembly in accordance with claim 4 and further including a valve disposed in said second conduit proximate said second tube distal end.

* * * * *